(12) United States Patent
Matsuda

(10) Patent No.: US 10,799,382 B2
(45) Date of Patent: Oct. 13, 2020

(54) CORRECTION APPARATUS

(71) Applicant: NAKAME, INC., Tokyo (JP)

(72) Inventor: Hiroshi Matsuda, Tokyo (JP)

(73) Assignee: NAKAME, INC., Tokyo (JP)

( * ) Notice: Subject to any disclaimer, the term of this patent is extended or adjusted under 35 U.S.C. 154(b) by 641 days.

(21) Appl. No.: 15/503,476

(22) PCT Filed: Aug. 14, 2015

(86) PCT No.: PCT/JP2015/072977
§ 371 (c)(1),
(2) Date: Feb. 13, 2017

(87) PCT Pub. No.: WO2016/024638
PCT Pub. Date: Feb. 18, 2016

(65) Prior Publication Data
US 2017/0231806 A1    Aug. 17, 2017

(30) Foreign Application Priority Data

Aug. 14, 2014  (JP) .................. 2014-165048
Apr. 28, 2015  (WO) ................. PCT/JP2015/062907

(51) Int. Cl.
*A61F 5/01* (2006.01)
*A61F 5/10* (2006.01)
(Continued)

(52) U.S. Cl.
CPC .............. *A61F 5/019* (2013.01); *A61F 5/01* (2013.01); *A61F 5/10* (2013.01); *A61F 5/37* (2013.01);
(Continued)

(58) Field of Classification Search
CPC .......... A61F 5/019; A61F 5/10; A61F 13/063; A61F 13/068; A61F 2013/0048
(Continued)

(56) References Cited

U.S. PATENT DOCUMENTS 7,458,946 B2 * 12/2008 Ryscavage ............ A61F 5/0118
602/20
8,690,810 B2 * 4/2014 Greenberg ............ A61F 5/0118
602/22
(Continued)

FOREIGN PATENT DOCUMENTS

JP          6-41730        6/1994
JP        H11-047203 A    2/1999
(Continued)

*Primary Examiner* — Keri J Nelson
(74) *Attorney, Agent, or Firm* — Renner, Otto, Boisselle & Sklar, LLP

(57) ABSTRACT

[Problem] To provide a correcting tool by which the center of the body is stabilized and/or a twist in the body is corrected by simply wearing the correcting tool in everyday life. [Solution] According to the present invention, the following invention is provided. (1) A tool for correcting a twist in the body is composed of a cylindrical material having elasticity with a diameter of 7-20 mm, a width 5-10 mm, a thickness of 1-3 mm, and a hardness of 4-6. According to the present invention, the tool of the present invention is worn to perform daily life activities or exercise, thereby stabilizing the center of the body and/or correcting a twist in the body.

8 Claims, 1 Drawing Sheet

(51) Int. Cl.
  *A61F 5/37*  (2006.01)
  *A61F 5/56*  (2006.01)
  A61F 13/06  (2006.01)
  A61F 13/00  (2006.01)

(52) U.S. Cl.
  CPC .............. *A61F 5/56* (2013.01); *A61F 13/068* (2013.01); *A61F 2013/0048* (2013.01)

(58) Field of Classification Search
  USPC ........... 602/22, 30, 63; 128/893, 894; 63/11, 63/15, 15.5, 15.9
  See application file for complete search history.

(56) References Cited

U.S. PATENT DOCUMENTS

| | | | |
|---|---|---|---|
| 9,066,790 B1 * | 6/2015 | Fisher | A61F 5/019 |
| 2010/0222728 A1 * | 9/2010 | Brooks | A61F 13/068 |
| | | | 602/30 |
| 2014/0267116 A1 * | 9/2014 | Weiner | A61F 5/05866 |
| | | | 345/173 |

FOREIGN PATENT DOCUMENTS

| | | |
|---|---|---|
| JP | 3061535 | 6/1999 |
| JP | 3089772 | 8/2002 |
| JP | 3737752 B2 | 1/2006 |
| JP | 2007-167122 A | 7/2007 |
| JP | 2009-254712 A | 11/2009 |

* cited by examiner

[Fig.1]
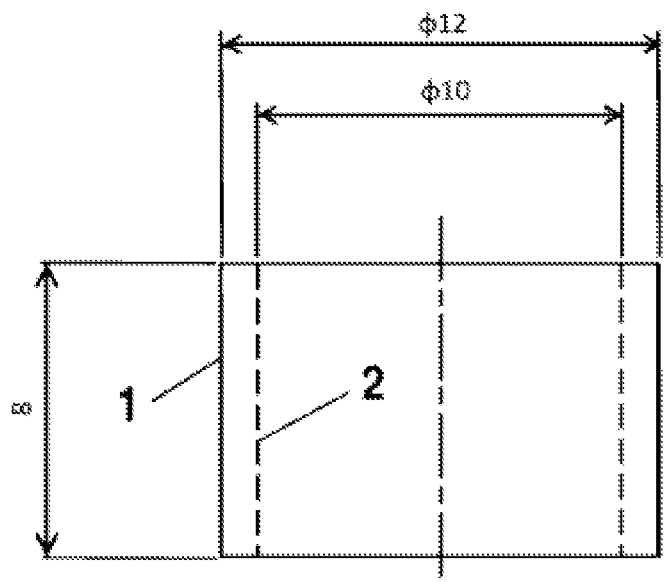
[Fig.2]
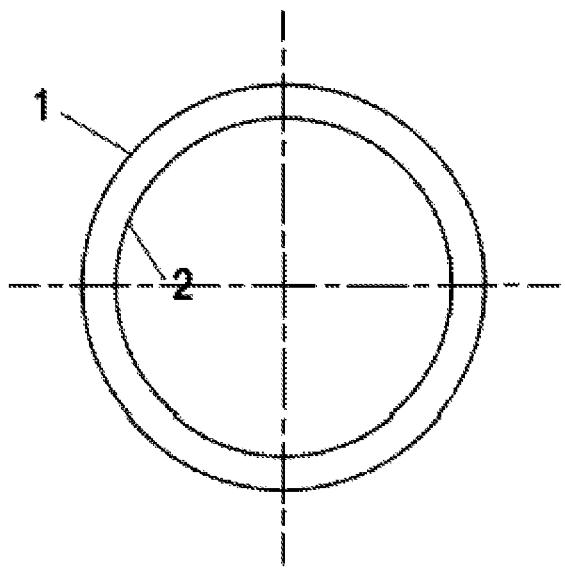

CORRECTION APPARATUS

TECHNICAL FIELD

The present invention relates to a correction tool correcting distortion of a body.

BACKGROUND ART

In recent years, with westernization of the life style, opportunities of sitting straight decreased in everyday life but they still remain to some extent. In addition, in recent years, opportunities that distortion of body occurs increase by increase of people who lack exercise with the development of transportation means and by doing desk work with an awkward position. If there is distortion of these bodies, the ground contact by the foot becomes unnatural, the position of the center of gravity shifts, and the distortion of the body may deteriorate in some cases.

As an apparatus for removing such body distortion, patent literature 1, patent literature 2 and patent literature 3 etc. had been developed but there is a problem to take time and money as every apparatus is fairly large and as it needs special time to exercise.

Therefore, to develop an tool to remove body distortion without taking special time only by wearing it and by living normally.

RELATED ART DOCUMENTS

Patent Documents

Patent literature 1: Japanese Unexamined Patent Application Publication No. 1111-047203
Patent literature 2: Japanese Utility Model No. 3061535
Patent literature 3: Japanese Patent No. 3737752

SUMMARY OF THE INVENTION

Problem to be Solved by the Invention

A tool is provided that stabilizes the center of gravity and/or corrects the distortion of the body by simply wearing and by living a normal life.

Means for Solving the Problem

According to the present invention, the following inventions are provided.

(1) A tool for correcting distortion of body, consisting of a cylindrical resilient material having a diameter of 7 to 20 mm, a width of 5 to 10 mm, a thickness of 1 to 3 mm, and a hardness of 4 to 6. Hardness means hardness measured by a hardness tester named type A durometer according to JIS K6253 standard. In addition, as a resilient material, for example, rubber, silicone rubber, and the like are listed, but the material is not limited thereto. Preferably it is silicone rubber. A diameter means an inner diameter.

(2) A tool according to (1), wherein said distortion of body is bow leg, distortion of the spine, distortion of the pelvis, deviation of the center of gravity, and flexibility. Flexibility refers to asymmetric flexibility such as being difficult to bend in one direction. It means the difference in flexibility depending on the direction such that front bending is considerably bent, but back flexion does not bend at all for example. This is thought to be caused by distortion of body.

(3) A tool according to (1) or (2), wherein the inner surface of the cylinder is embossed.

(4) A tool according to (1) to (3), wherein supporting surface of a foot and the ground is stabilized.

(5) A tool according to (1) to (4), characterized in that flexibility of body is increased by wearing it.

(6) A correction tool for body distortion consisting of a cylindrical resilient material having a diameter of 7 to 20 mm, a width of 5 to 10 mm, a thickness of 1 to 3 mm, and a hardness of 7 to 30.

(7) A correction tool for body distortion according to (1) to (6), which is a correction tool for snoring reduction.

(8) A method for correcting body distortion, wherein body distortion is corrected by wearing a correction tool consisting of a cylindrical resilient material having a diameter of 7 to 20 mm, a width of 5 to 10 mm, a thickness of 1 to 3 mm, and a hardness of 4 to 6 at least more than one appropriate toe. The correction tool is preferably that described in (1) to (5) above. An appropriate toe means a toe which improves body distortion or flexibility.

(9) A method according to (8), wherein said body distortion is bow leg, distortion of the spine, distortion of the pelvis, deviation of the center of gravity, or flexibility.

(10) A method according to (8) or (9), wherein the inner surface of the cylinder is embossed.

(11) A method according to any one of (8) to (10) wherein the said correction tool stabilizes supporting surface of a foot and the ground.

(12) A method described in any one of (8) to (11), characterized in that the said correction tool increases flexibility of body by wearing it.

(13) A method according to any one of (8) to (12) wherein the said correction tool consists of a cylindrical resilient material having a diameter of 7 to 20 mm, a width of 5 to 10 mm, a thickness of 1 to 3 mm, and a hardness of 7 to 30.

(14) A method for improving snoring, using any of the correction tool according to (1) to (6).

(15) A method for improving body flexibility using any of the correction tool according to (1) to (6).

(16) The correction tool according to (1) to (6) for use in correction of body distortion.

(17) A correction tool according to (1) to (6), for use in prevention or treatment of body distortion.

(18) A kit comprising two or more correction tools comprising more than any one kind of correction tools or correction tools for two or more kinds of different fingers comprising at least more than 1 correction tool in the group consisting of correction tools for a thumb, a forefinger, a middle finger, a ring finger and a little finger.

Effects of the Invention

According to the present invention, the center of gravity can be stabilized and/or body distortion can be corrected by wearing the present tool and by living a usual life or by exercising exercise etc.

BRIEF DESCRIPTION OF DRAWINGS

FIG. 1 is a figure of side view of the cylindrical correction tool for a middle finger of a foot of the present invention. The dot shows inner wall of the cylinder.

FIG. 2 is a figure viewed from upper direction of the cylindrical correction tool of the present invention.

DESCRIPTION OF EMBODIMENTS

The correction tool of the present invention is a cylindrical tool consisting of elastic material. The size is not particularly limited, but those having a diameter of 7 to 20 mm, a width of 5 to 10 mm, a thickness of 1 to 3 mm, and a hardness of 4 to 6 are preferably used. More preferably, it has a diameter of 8 to 16 mm, a width of 6 to 8 mm, a thickness of 2 mm and a hardness of 5, but for larger people or foreigners, it may be larger than this. A basic form is shown in FIG. 1 and FIG. 2. A basic shape is preferably a perfect circle or a shape close thereto. It is preferable to carry out non-slip processing such as embossing inside (inside the cylinder). In the present specification, the diameter means the diameter of the inner diameter, unless particularly specified.

The correction tool of the present invention is preferably worn on the toes. In that case, the diameter of the correction tool of the present invention can be varied by the thickness of the toes. A preferable inner diameter is 14 to 18 mm, more preferably 15 to 17 mm, and most preferably 16 mm in the case of the thumb of the foot.

For the correction tool of the present invention to be worn on a forefinger, a middle finger and a ring finger of the foot, the preferable inner diameter is 7 to 13 mm, more preferably 8 to 12 mm, further preferably 9 to 11 mm, most preferably 10 mm.

For the correction tool of the present invention to be worn on a little finger of the foot, the preferable inner diameter is 5 to 11 mm, more preferably 6 to 10 mm, further preferably 7 to 9 mm, most preferably 8 mm. With respect to these inner diameters, it can be used by appropriately modifying it according to the physical difference of individuals.

Elastic materials include, but are not limited to various elastomer resins such as urethane resin, butadiene rubber, styrene-butadiene rubber, chloroprene rubber, natural rubber, silicone gel, silicone rubber, acrylic rubber, styrene rubber and the like. Among these, silicon rubber is particularly preferable in consideration of wearing feeling, color and the like. What is essential is material that has moderate pressure when worn on a toe, and has elasticity to the extent that it does not matter even if it is worn all day. In addition, the material is not limited to one kind, and a plurality of combinations may be used.

An elastic material may contain an antibacterial agent. As antibacterial agents, an antibacterial agent well known to those skilled in the art can be used, and there is no particular limitation but for example, a silver type antibacterial agent (such as zeolite zirconium, apatite, titania or the like carrying silver ions, etc.) can be used. The antibacterial agent is preferably blended in an amount of from 0.01 to 10% by weight, more preferably from 0.1 to 5% by weight, based on the total rubber component.

Here, "consisting of an elastic material" does not mean that it does not include any material that does not have elasticity in that but means that it contains a material having elasticity as a main component. Materials that do not have elasticity in part may be contained.

As color, transparent to semi-transparent color is preferable, and in case of coloring, colors that are close to skin color and less noticeable are preferable, but colors are not limited to these. For example, for use as fashion, colorful objects and patterns may be added.

In the correction tool of the present invention, the entire cylindrical surface of the cylindrical shape may be continuous or may have a hole like a mesh shape. In essence, as long as wearing and correcting the distortion of the body, the shape of the cylinder is not particularly limited The correction tool of the present invention is used by wearing it to one or more of a toe, that is, a thumb, an index finger, a middle finger, a ring finger, and a little finger of a foot. At this time, although they may be worn symmetrically in some cases, they may be worn asymmetrically depending on the patient's case. Also, the number of tools to be worn may not be the same, for example one may be attached to the right foot, and three to five to the left foot, etc.

To decide on which finger to be worn, it is preferable to wear it on the finger that changes the flexibility etc. of the body when it is worn actually. For example, it is preferable to wear it on the toe for which side hand of the person is hard to stick to the floor when bending forward. In short, it may be worn on the toes that the person felt the effect such as increased flexibility by wearing.

Normally, they are worn on the toes of both feet, selected and worn not on all toes but on particularly effective toes. According to the tendency of distortion of the body, it is also effective to receive advice from experts who know empirically as to which fingers to wear.

The correction tool of the present invention exerts a different influence depending on which toe a wearer wears. For example, if a wearer wears it as followings, it becomes easier to do the hard action; it is worn on the little finger when it is difficult to make a forward bending action; it is worn on the index finger when the back flexing work is difficult to do; it is worn on the ring finger when the side bending action is difficult to do; it is worn on the thumb when the inner turning work of the leg is difficult to do; it is worn on the middle finger when it is difficult to perform the rotation motion of upper part of the body is difficult to do.

A case to which the correction tool of the present invention is applied is not particularly limited, but it is preferably applied to the people who have cases such as deviation of gravity center, low flexibility of body, joint pain of the knee, bow-legs, knock-knees, distortion of a spine, distortion of a cervical spine, and low back pain. The distortion of the body can be easily found as the midline shifts by observation in an upright state. When the center of gravity is deviated, the center line of the body shifts to the left or right from the midline. In addition, whether the center of gravity is deviated or not can be judged by inserting a paper such as a card on the bottom of the foot depending on whether there is a gap or not. By observing these, it is possible to select an appropriate toe for wearing the correction tool of the present invention.

The correction tool of the present invention has the effect that the whole sole is weighted, that the center of gravity is stabilized, and that therefore, the distortion of the body is corrected, because the degree of application of force to the toes can be adjusted. Therefore, flat feet, valgus thumb and fingers etc. can also be corrected. In addition, the effect of reducing the snoring was also seen by wearing the correction tool of the present invention.

The correction tool of the present invention exerts a certain effect even if it is worn so as to cover the middle phalangeal bone, the distal phalanx and/or the joint of the finger, but it is more preferable to wear it around the basal bone. That is, it is preferable that the correction tool of the present invention is worn between the base of the toes and/or the fingers of the hands and the joints closest to the root, and it is not necessary to cover the joints of the fingers.

By continuing to press a part from the base of the finger to nearest part of the joint closest to the base with the strength not to be felt, the effects of unconsciously reducing the bias and distortion of the center of gravity, and of reducing or eliminating pain accompanying it are obtained. Examples of the pain alleviated by wearing the correction tool of the present invention include, but are not limited to, knee pain, lower back pain, hip joint pain, back pain, shoulder pain, neck pain, and the like.

The correction tool of the present invention can also be used for athletes. When an athlete suffers an injury or breaks, the center of gravity is shifted, but in that case, a correction tool for the athlete may be used. The correction tool for an athlete has the same shape as the ordinary one but the hardness is harder than usual, 7 to 30, more preferably 8 to 29, further preferably 10 to 27, even more preferably 12 To 25, particularly preferably from 15 to 25, and most preferably from 18 to 22. In the case of athletes, the reason why the hardness was increased is to make it hard to break even if it makes intense movements with rugby or the like. Therefore, the hardness may be decreased to an extent such that it can not be cut depending on the severity of the movement of the sports. For example, the upper limit of the hardness of the correction tool of the present invention can be 20 or less, 19 or less, 18 or less, 17 or less, 16 or less, 15 or less, 14 or less, 13 or less, 12 or less, 11 or less, 10 or less, 9 or less, 8 Hereinafter, it may be reduced to 7 or less.

In the case of athletes, the correction tool of the present invention can also be used to correct body distortion. Distortion of the body includes, but is not limited to, bow-legs, distortion of the spine, distortion of the pelvis, deviation of the center of gravity, and the like. Furthermore, effects such as improvement of flexibility and improvement of exercise capacity were seen.

It is possible that a so-called acupressure point and a meridian may be involved although the mechanism by which the correction tool of the present invention exerts its effect has not yet been elucidated sufficiently.

EXAMPLES

Example 1

A woman who kept sitting at desk work almost all day, felt heavy in her leg (calf) in the afternoon and had a habit to sit straight on the chair everyday. So, the correction tool of the present invention was worn on the toes throughout the day and her legs became easier not to need to sit straight. The wearing pattern was to wear on the left foot thumb L size (inner diameter of 1.6 cm), the left foot middle finger M size (inner diameter of 1.0 cm), and right leg ring finger M size, right foot little finger S size (inner diameter of 0.8 cm). After that she wears them every day.

In the case of this woman, as a result of wearing them every day, the following effects were observed.

(1) Discomfort in her back was eliminated.

This was her long-standing trouble, she felt something stiff around the middle of her back and waist and it was very uncomfortable. However, after wearing them every day for a while, she felt no discomfort, even if she warped backwards during the morning radio gymnastic exercise in her company.

At the end of the day she felt very dull, she did not decide sleep posture at all, she was always in a shallow state of sleep, but now she can sleep well at night, so she can feel the refreshing feeling.

(2) The heaviness of the foot has gone away.

The calf's heaviness in the afternoon has disappeared. After 4 weeks of wearing them, it became possible to spend without sitting straight at the company.

In addition, it became hard to feel heaviness of the legs during commute time to work (2 transfers, standing for total one hour).

These effects are considered to be the effect of stabilizing grounding of the toes, correcting the distortion of the body, and stabilizing the center of gravity as a result of wearing the correction tool of the present invention. The correction tool of the present invention is characterized by the continuous correction of distortion of the body in the course of action in work and in everyday life with continuous wearing. Therefore, it is preferable that it has such hardness, elasticity, and shape (cylindrical shape) that wearing it is not felt to consciousness. Also, a shape that allows the user to be conscious of being worn is not preferable due to protrusions or the like, and a cylindrical shape having no projection on the surface is preferable. Further, a shape that does not give a sense of incompatibility even when it is worn under socks or shoes is preferable. That is, it is preferable that a shape can exert a therapeutic effect without awareness of wearing even when wearing it all day or even when wearing it during sleeping. Also, the correction tool is not always necessary to touch the belly of the finger, and it is effective if it is in contact with the indirect part.

Example 2

A patient case, with a stern back, who has no particular subjective symptoms besides occasional backache. In the state before wearing the correction tool of the present invention, the forward bending was such that the fingertip was attached, and the back flexion did not bend at all only with the head being upward. A card was used to check the deviation of the center of gravity (whether she captures the ground with the whole soles of the feet) at the sitting position and standing position. Various ways to wear the correction tool of the present invention on the toes were tried to decide the best way of wearing.

When the correction tool of the present invention is worn, the anterior bending became not to bent by a couple of centimeters, but in the case of backbending, the person herself was surprised to bend backwards so much. The person herself was also surprised that the humpback was improved much by looking at the mirror.

Example 3

A case of a patient who is concerned about the chubbiness inside the thigh. The inside of the thigh became slimmed-down just by walking with wearing the correction tool of the present invention without other stretch or muscle training.

When wearing it on the hand, as the left shoulder which had been rolled up became straightened, as well as the muscles of the left front chest, the left upper arm, especially the front side of the arm became sore. It is possible that such symptoms appear because ribs are twisted and warped.

Example 4

When a man in his 50s with bow-legs was worn with the correction tool of the present invention on the middle finger of the left foot, and on the thumb, the middle finger, and the ring finger of the right foot and maintained for one month, the knees of the bow-legs become to make a cracking sound when walking. He continued after that and the bow-legs were corrected considerably. In such a case, it may be more effective to change the position of the toes on which the correction tool is worn in order to further enhance the effect when an effect comes out.

Example 5

A girl in the fifth grade of elementary school who is doing ballet, with a center of gravity on the right foot side and with distortion causing difficulty to sidebend to the right and to rotate to the left, wore the correction tool of the present invention on toes (left foot ring finger and right foot middle finger) to practice except in sleeping and bathing, the distortion of the body was improved and progressed remarkably to be ranked 9th nationwide after two months, second after four months, nation first after five months. By wearing the correction tool of the present invention, the effect of improving ballet movement was seen.

When a professional rugby player wore the correction tool of the present invention on the left foot thumb and on the right foot ring finger after the game, inner tightness was disappeared although he had the pain of the knee bruises. Moreover, he could feel that the distortion of the back was corrected.

Another rugby player had the weak right ankle, whose weight was on the outside of the upper part of the foot regarding the balance of the body and his weight was not on the ball of the thumb. When the toe band was worn on the right foot thumb and on the right foot index finger, the center of gravity of the body was loaded forward and the weight was properly applied on the ball of the thumb.

When a man with terrible snoring wore the correction tool of the present invention on the middle finger of both feet to sleep, snoring was obviously improved. It seems that breathing became easier and snoring was alleviated because the body became straight.

Since the correction tool according to the present invention is to be worn on the toes according to the symptoms of each person on the left and right toe, it is common to use a plurality of correction tools in combination. Therefore, as a sales form, it can be sold as a single item, but it can also be sold in the form of combination kit. For example, it may be a kit including at least one combination selected from the group consisting of thumb and middle finger, middle finger and little finger, and little finger and thumb, and a kit may contain all correction tools for thumb, middle finger and little finger. Furthermore, a kit including two or more correction tools of any one or more types selected from the group consisting of correction tools for a thumb, an index finger, a middle finger, a ring finger, and a little finger, or a kit including correction tools of two or more different kinds among those can be sold as a kit containing a combination of correction tools. It can also be sold as a kit containing all of these five types, or as a kit containing two or more of five types.

INDUSTRIAL APPLICABILITY

The present invention can be used in the health industry, the manufacturing industry of health equipment, and the like.

DESCRIPTION OF THE REFERENCE NUMERALS 1 outer circumference of a cylinder
2 inner circumference of cylinder

The invention claimed is:

1. A method for correcting body distortion, comprising:
    a step of determining a toe of a person on which a correction tool is to be worn based on a change in flexibility of a body of the person when the correction tool is worn, and
    a step of wearing the correction tool on the toe of the person to correct body distortion,
    wherein the correction tool consists of a cylindrical resilient material having a diameter of 7 to 20 mm, a width of 5 to 10 mm, a thickness of 1 to 3 mm, and a hardness of 4 to 6.

2. The method according to claim 1, wherein the step of determining the toe of the person on which the correction tool is to be worn comprises:
    determining which hand of the person is hard to stick to the floor when bending forward; and
    selecting the toe from a foot of the person on a side of the person having the hand that is hard to stick to the floor when the person is bending forward, wherein:
        the toe on which the correction tool is worn is a little toe of the person when it is difficult for the person to make a forward bending action;
        the toe on which the correction tool is worn is an index toe of the person when it is difficult for the person to make a back flexing action;
        the toe on which the correction tool is worn is a ring toe of the person when it is difficult for the person to make a side bending action;
        the toe on which the correction tool is worn is a thumb toe of the person when an inner turning of the leg of the person is difficult.

3. The method according to claim 2, wherein said body distortion is bow leg, distortion of the spine, distortion of the pelvis, deviation of the center of gravity, or flexibility.

4. The method according to claim 1, wherein the inner surface of the cylindrical resilient material is embossed.

5. The method according to claim 4 wherein the said correction tool stabilizes supporting surface of a foot and the ground.

6. The method described in claim 1, wherein the said correction tool increases flexibility of body by wearing it.

7. The method according to claim 1, wherein the step of determining the toe of the person on which the correction tool is to be worn comprises wearing the correction tool to determine the toe that when the correction tool is worn thereon changes a flexibility of a body of the person.

8. The method according to claim 1, wherein one or more additional correction tools are worn on one or more other toes of the person, each additional correction tool being worn on a respective one of the other toes, the one or more other toes on which the one or more additional correction tools are respectively worn determined based on a change in flexibility of the body of the person when the one or more additional correction tools are worn,
    wherein each of the additional correction tools consists of a cylindrical resilient material having a diameter of 7 to 20 mm, a width of 5 to 10 mm, a thickness of 1 to 3 mm, and a hardness of 4 to 6.

* * * * *